(12) United States Patent
Burz et al.

(10) Patent No.: US 9,242,063 B2
(45) Date of Patent: Jan. 26, 2016

(54) FOREHEAD-CONTACTING DEVICE FOR A BREATHING MASK AND METHOD FOR MAKING THE SAME

(71) Applicant: ResMed R&D Germany GmbH, Martinsried (DE)

(72) Inventors: Johann S. Burz, Germaringen (DE); Achim Biener, Aufkirchen (DE); Bernd C. Lang, Grafelfing (DE)

(73) Assignee: RESMED R&D GERMANY GMBH, Martinsried (DE)

( * ) Notice: Subject to any disclaimer, the term of this patent is extended or adjusted under 35 U.S.C. 154(b) by 0 days.

(21) Appl. No.: 13/862,790

(22) Filed: Apr. 15, 2013

(65) Prior Publication Data

US 2014/0130337 A1   May 15, 2014

Related U.S. Application Data

(63) Continuation of application No. 11/988,447, filed as application No. PCT/EP2006/007119 on Jul. 19, 2006, now Pat. No. 8,439,040.

(30) Foreign Application Priority Data

Jul. 19, 2005  (DE) .......................... 10 2005 033 649

(51) Int. Cl.
  *A61M 16/06* (2006.01)
(52) U.S. Cl.
  CPC ........... *A61M 16/0683* (2013.01); *A61M 16/06* (2013.01); *A61M 16/0633* (2014.02); *Y10T 29/49993* (2015.01)

(58) Field of Classification Search
  CPC ............ A61M 16/0683; A61M 16/06; A61M 16/0633
  USPC ........... 29/530; 128/206.21, 206.24; 156/146; 264/267
  See application file for complete search history.

(56) References Cited

U.S. PATENT DOCUMENTS

| | | | |
|---|---|---|---|
| 2,343,512 A | | 3/1944 | Lobl |
| 2,749,910 A | * | 6/1956 | Faulconer, Jr. .................. 601/44 |
| 2,875,757 A | * | 3/1959 | Galleher, Jr. ............. 128/206.26 |
| 3,162,974 A | | 12/1964 | Jackson et al. |
| 4,332,634 A | | 6/1982 | Aperavich |
| 4,966,568 A | | 10/1990 | Nakamura et al. |

(Continued)

FOREIGN PATENT DOCUMENTS

| | | |
|---|---|---|
| DE | 100 45 183 A1 | 5/2002 |
| EP | 41268 A1 | 12/1981 |

(Continued)

OTHER PUBLICATIONS

International Search Report for PCT/EP2006/007119 mailed Nov. 9, 2006.

(Continued)

*Primary Examiner* — David Bryant
*Assistant Examiner* — Ruth G Hidalgo-Hernandez
(74) *Attorney, Agent, or Firm* — Nixon & Vanderhye, P.C.

(57) ABSTRACT

A forehead-contacting device for a breathing mask includes a support element made from an elastomer material. The support element forms a support face which in an application position is adapted to seat on a forehead area of a user. The support element includes a jacket that defines a hollow chamber adapted to be filled with a viscous medium.

23 Claims, 7 Drawing Sheets

(56) References Cited

U.S. PATENT DOCUMENTS

| | | | |
|---|---|---|---|
| 5,079,786 | A | 1/1992 | Rojas |
| 5,119,842 | A | 6/1992 | Jaw |
| 5,391,248 | A * | 2/1995 | Brain .......................... 156/242 |
| 5,522,757 | A | 6/1996 | Ostrowski |
| 6,467,483 | B1 | 10/2002 | Kopacko et al. |
| 6,494,206 | B1 * | 12/2002 | Bergamaschi et al. .. 128/206.24 |
| 7,036,803 | B2 | 5/2006 | Maas et al. |
| 7,146,934 | B1 | 12/2006 | Staley |
| 7,252,213 | B1 | 8/2007 | DeSanto |
| 2001/0025641 | A1 * | 10/2001 | Doane et al. ............. 128/207.15 |
| 2005/0011522 | A1 | 1/2005 | Ho et al. |
| 2005/0199239 | A1 | 9/2005 | Lang et al. |
| 2009/0277453 | A1 | 11/2009 | Burz et al. |

FOREIGN PATENT DOCUMENTS

| | | |
|---|---|---|
| GB | 790677 | 2/1958 |
| GB | 2066097 A | 7/1981 |
| WO | WO 98/48878 | 11/1998 |
| WO | WO 99/58198 | 11/1999 |
| WO | WO 03/035156 A2 | 3/2003 |
| WO | WO 03/105921 A2 | 12/2003 |

OTHER PUBLICATIONS

Written Opinion of the International Searching Authority for PCT/EP2006/007119.

First Office Action issued in related DE Application No. 10 2005 033 649.3 dated Jan. 19, 2015 with English translation, 15 pages.

\* cited by examiner

FOREHEAD-CONTACTING DEVICE FOR A BREATHING MASK AND METHOD FOR MAKING THE SAME

CROSS-REFERENCE TO RELATED APPLICATION

This application is a continuation of U.S. patent application Ser. No. 11/988,447 filed Jan. 8, 2008, which is the U.S. national phase of International Application No. PCT/EP2006/007119 filed Jul. 19, 2006, which designated the U.S. and claims the benefit of German Patent Application No. 10 2005 033 649.3, filed Jul. 19, 2005, the entire contents of each which are hereby incorporated by reference in this application.

FIELD OF THE INVENTION

The present invention relates to a forehead-contacting device for a breathing mask.

BACKGROUND OF THE INVENTION

From International Patent Disclosure WO 2003/035156 incorporated herein by reference in its entirety, a forehead-contacting device for a breathing mask is known, which includes two pads made from a solid elastomer material. The two pads are secured to a forehead support incorporated adjustably into the breathing mask. The pads make it possible to support a corresponding breathing mask relatively comfortably on the forehead of a user of the mask.

SUMMARY OF THE INVENTION

One aspect of the invention is to provide additional advantages in terms of comfort for the user of breathing masks.

One aspect of the invention relates to a forehead-contacting device for a breathing mask including a support element made from an elastomer material. The support element forms a support face which in an application position is adapted to seat on a forehead area of a user. The support element includes a jacket that defines a hollow chamber adapted to be filled with a viscous medium.

As a result, it may be advantageously possible to support the forehead-contacting device in a way that is improved in terms of the distribution of pressure per unit of surface area and the adaptability of the forehead-contacting device.

In an embodiment of the invention, the jacket of the support element may be filled with a medium that is viscous and gelatinous or gel-like or cross-linked, e.g., silicone rubber. The jacket may be relatively thin-walled, e.g., with a wall thickness of 0.8 mm. The thickness may vary. By adapting the thickness of the jacket, it may be possible to exert an influence on the mechanical properties of the forehead-contacting device.

The jacket may be structured such that the forehead-contacting device, formed with the jacket, may be incorporated in a tilting or tumbling joint fashion (e.g., like a universal joint) to a certain extent into the breathing mask. The jacket may be structured such that it has an essentially mushroom-shaped design. The top or bottom of the mushroom may form the support face that faces toward the user in the application position and rests on the user's forehead.

The jacket of the support element may be structured such that, when viewed from a direction substantially perpendicular to the support face, it is contoured circularly. As an alternative, the jacket may be structured such that the jacket contour is substantially polygonal or crescent-shaped.

The jacket may include a neck or shaft region that is markedly tapered, compared to the portion that forms the support face. The neck or shaft region may be provided with a closure device. The closure device may be made from a relatively rigid material and form part of a fastening device for incorporating the support element into the breathing mask.

The closure device may be structured in multiple parts and may include both a collar element and a closure plug element that can be inserted into the collar element. The collar element and the closure plug element may be structured such that they form a spreading or clamping structure by which the neck or shaft region of the jacket, which penetrates the collar element, is clamped sufficiently firmly and in a sealing fashion and closed. The closure plug element may function as a plug, by way of which a plug hole, provided for filling the interior of the jacket, is sealed off.

The jacket may be made from a fully transparent elastomer material, e.g., liquid silicone rubber (LSR). The viscous medium intended for filling the jacket may be colored in some way that is aesthetically appealing. It is furthermore possible to incorporate air bubbles into the viscous medium. It is also possible to provide small decorative inclusions in the viscous medium, e.g., miniaturized living creatures, fish, or frogs, or such things as snowflakes or stars.

The jacket may be made in cooperation with a mold core tool. The unmolding of the mold core tool may be done by elastically widening the jacket, e.g., by pulling the mold core tool out along the inner region of the neck or shaft portion of the jacket.

The neck or shaft region of the jacket may be designed such that it can be sufficiently widened elastically. The core tool may be structured in multiple parts, e.g., a folding core. Unmolding the jacket from the mold core tool may be done by blowing the jacket out from the mold core tool using a pressure medium. It is also possible to perform the unmolding from the mold core tool directly, e.g., by filling the jacket and in the process positively displacing the jacket from the mold core tool.

Filling the support element and its closure may be done in the context of a fully automated assembly operation. In an embodiment, the jacket may be delivered from an assembly structure in which the closure collar element is already located. After the shaft of the jacket is inserted into the collar element, a closure plug embodied as a filling conduit may be inserted partway into the collar element. Next, the interior of the jacket may be evacuated. After that, the jacket may be filled with an appropriate viscous medium, e.g., silicone gel. Next, the filled jacket may be closed completely by inserting the closure plug all the way in. In the context of this closure operation, the shaft of the jacket may be clamped in a sealing manner in the collar element.

The forehead-contacting device may be structured such that it forms a contact area in the range of at least 2 $cm^2$. It is possible to provide contours, in the region of the support face intended for contacting the user, that prevent the forehead-contacting device from being sucked against the forehead of the user.

Another aspect of the invention relates to a forehead-contacting device for a breathing mask. The forehead-contacting device includes a support element made from an elastomer material. The support element forms a support face which in an application position is adapted to seat on a forehead area of a user. The support element includes two jacket portions coupled to one another via a central connecting rib. Each of the jacket portions defines a hollow chamber adapted to be filled with a viscous medium.

Another aspect of the invention relates to a method for forming a forehead-contacting device. The method includes molding a support element form an elastomer material that includes a jacket defining a hollow chamber, and filling the hollow chamber with a viscous medium.

Another aspect of the invention relates to a method for forming a forehead-contacting device. The method includes molding a support element form an elastomer material that includes a jacket defining a hollow chamber, attaching a collar element to a shaft portion provided to the jacket, inserting a closure plug element including a core conduit at least partway into the collar element, filling the hollow chamber with a viscous medium via the core conduit of the closure plug element, and further inserting the closure plug element into the collar element to close core conduit and hence close the hollow chamber of the jacket.

Other aspects, features, and advantages of this invention will become apparent from the following detailed description when taken in conjunction with the accompanying drawings, which are a part of this disclosure and which illustrate, by way of example, principles of the invention.

BRIEF DESCRIPTION OF THE DRAWINGS

The accompanying drawings facilitate an understanding of the various embodiments of this invention. In such drawings:

FIG. 5b is a sectional view illustrating the functioning of the closure system shown in FIG. 5a;

DETAILED DESCRIPTION OF ILLUSTRATED EMBODIMENTS

Figure 1:
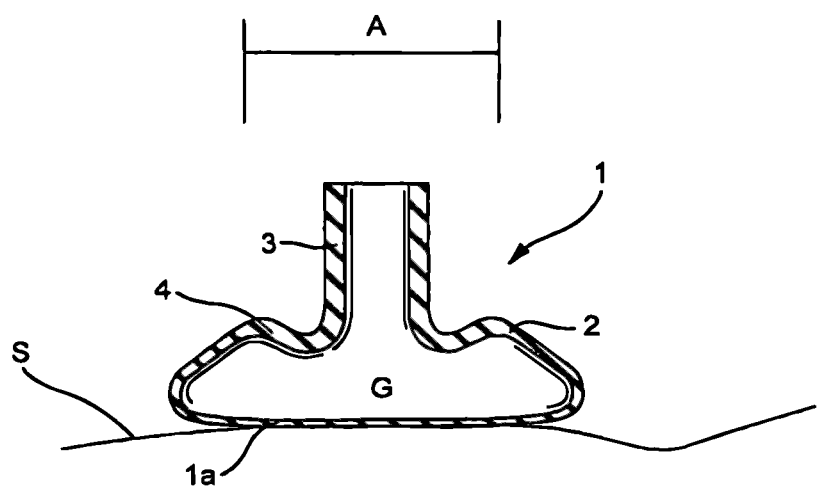
FIG. 1 is an axial section view illustrating a forehead-contacting device according to an embodiment of the invention.
Figure 9:
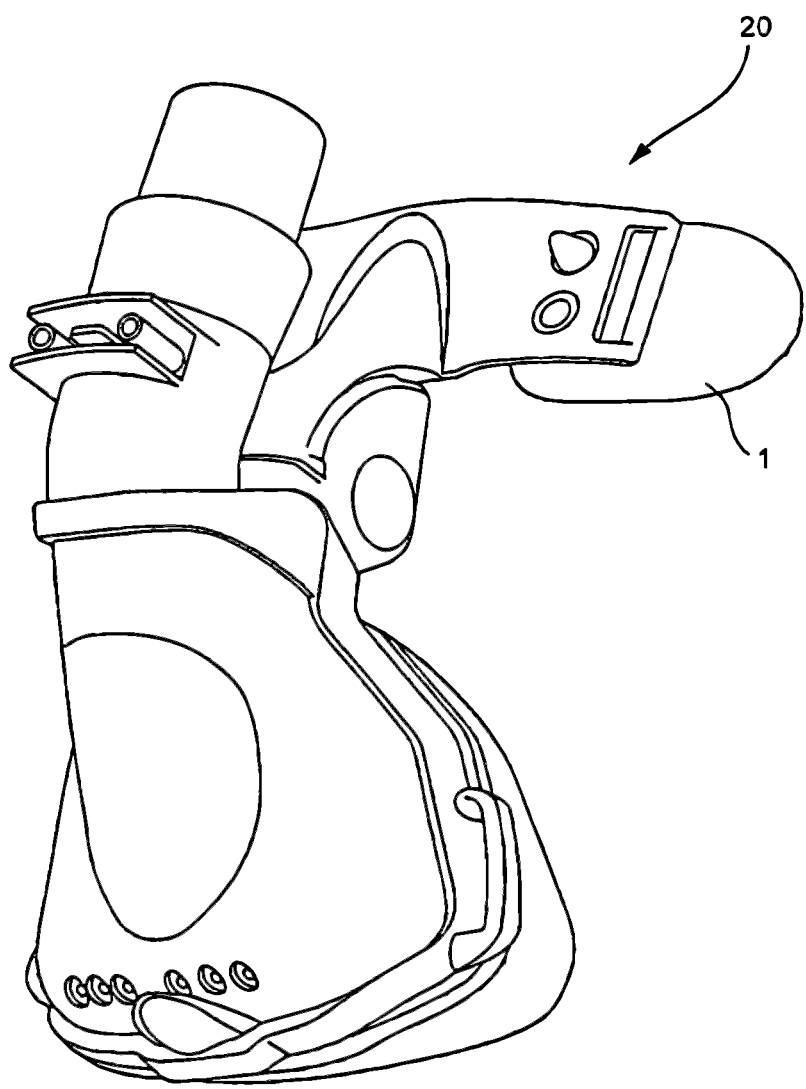
FIG. 9 is a perspective view of a breathing mask including a forehead contacting device according to an embodiment of the invention.

FIG. 1 shows a support element 1, made of an elastomer material, for a forehead-contacting device of a breathing mask (the breathing mask shown in FIG. 9 and also shown in WO 2003/035156, the entirety of which is incorporated herein by reference). The support element 1 forms a support face 1a, which in the application position is seated on a forehead area S of a user. The support element 1 includes a jacket 2, which defines a hollow chamber that is filled with a viscous medium G in such a way that the wall portion that forms the support face 1a is subjected, on its side facing away from the forehead area S of the user, essentially to the pressure of the viscous medium G. The jacket 2 is structured such that it surrounds a shaft portion 3 and an annular piston portion 4 that adjoins the shaft portion 3. The annular piston portion 4 and the inner region outlined by it define a piston area A, e.g., which is preferably smaller than the support face 1a that contacts the forehead area S of the user.

Figure 2:
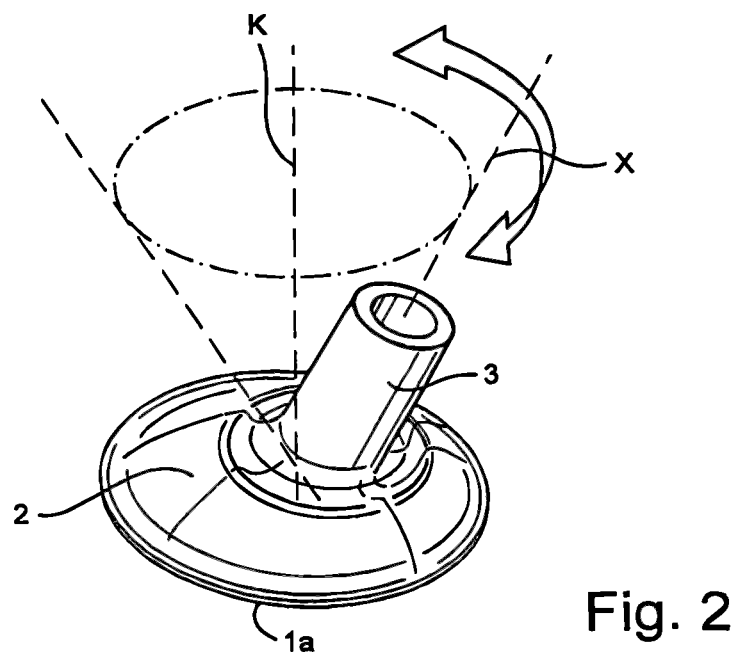
FIG. 2 is a perspective view illustrating a mechanical property of the forehead-contacting device having a jacket as shown in FIG. 1.

As can be seen from FIG. 2, the jacket 2 may be designed such that the shaft 3 is movable and provides a tilting or tumbling joint (e.g., like a universal joint) relative to the support face 1a. In particular, the axis X of the shaft 3 may be movable within a cone that is concentric to the primary axis K of the support face 1a. The angle of the tip of this cone may be in the range from 8 to 60°, for example.

Figure 3:
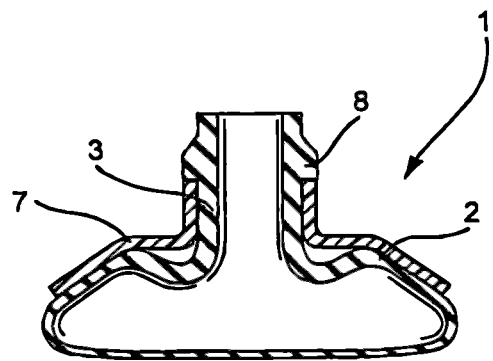
FIG. 3 is an axial sectional view illustrating a forehead-contacting device according to another embodiment of the invention, with the forehead contacting device having an integrated, essentially rigid support plate element.

FIG. 3 shows a variant of the support element 1 in which the jacket 2 is additionally braced or supported by a support plate element 7. The support plate element 7 may be fixed on an annular bead 8, which may be embodied on the shaft 3.

Figure 4:
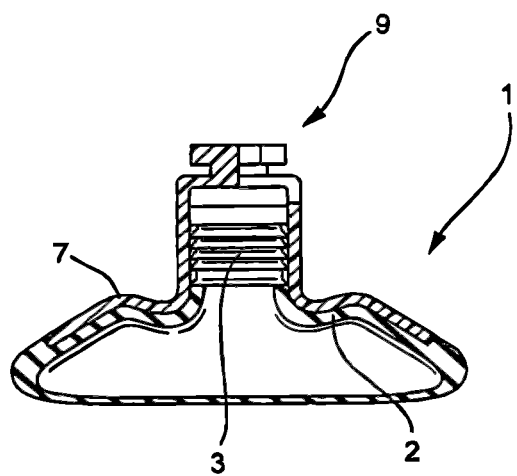
FIG. 4 is an axial sectional view of a forehead-contacting device, having a support plate element according to another embodiment of the invention.

FIG. 4 shows a variant of the support element 1 in which the support plate element 7 additionally forms a fastening structure or fastener 9, by way of which the support element 1 may be incorporated into or otherwise coupled or provided to a breathing mask. In this exemplary embodiment, the jacket 2 may be inserted via the shaft portion 3 into the support plate element 7.

Figure 5A:
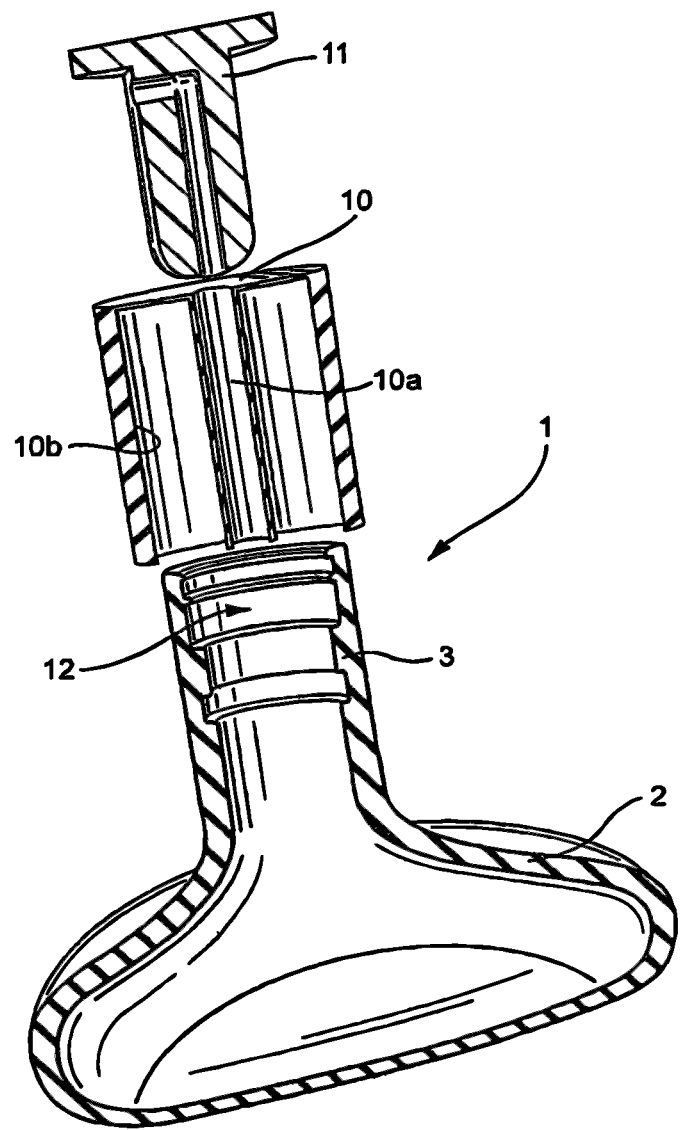
FIG. 5a is a sectional view illustrating a forehead-contacting device according to another embodiment of the invention, including the closure system intended for closing the hollow jacket.

FIG. 5a is an exploded view that illustrates the jacket 2 of the support element 1 along with an associated closure device. In the illustrated embodiment, the closure device includes a collar element 10 and a closure plug element 11 that can be inserted into the collar element 10. The collar element 10 is structured such that the shaft portion 3 of the jacket 2 can be inserted into it. The collar element 10 includes an inner expandable shaft 10a, by way of which, in cooperation with the closure plug element 11, the shaft portion 3 of the jacket 2 can be clamped from the inside against an inner circumferential wall 10b of the collar element 10. Profiled features, e.g., undercuts 12, may be provided in the internal region of the shaft portion 3 of the jacket 2 that serve to increase the security against the jacket 2 being pulled off in the installed state. In an embodiment of assembly, the collar element 10 may be first slipped onto the shaft portion 3. Next, the closure plug element 11 may be forced at least partway into the collar element 10.

Figure 5B:
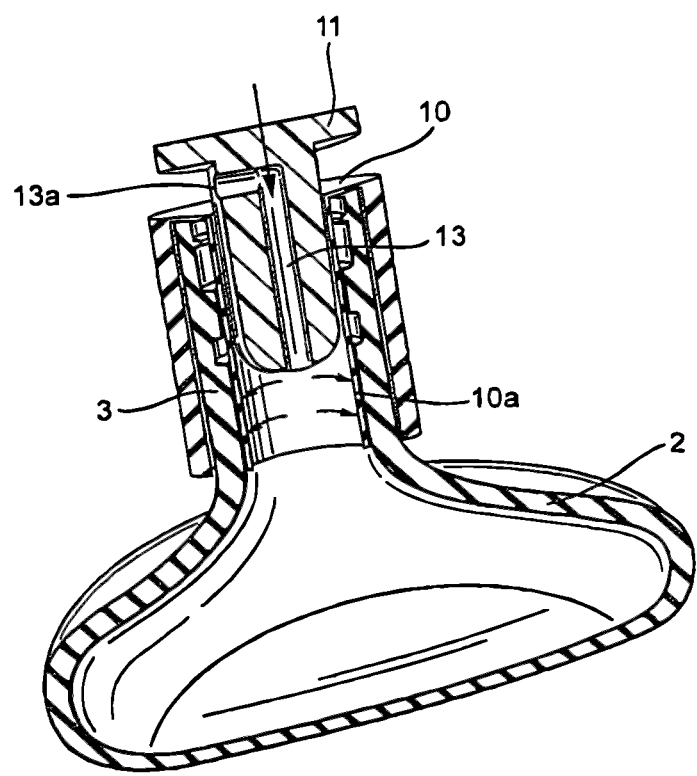

FIG. 5b shows a partially assembled state of the jacket and closure device shown in FIG. 5a. In this state, e.g., in a fully automated way, the inner region of the jacket 2 can be evacuated via the core conduit 13 in the closure plug element 11. Next, likewise via the core conduit 13, a viscous medium, e.g., silicone gel, intended for filling the interior of the jacket can be introduced into this inner region. Once the interior of the jacket 2 has been sufficiently filled, the closure plug element 11 may be forced all the way into the collar element 10. In the process, the outer orifice region 13a of the core conduit 13 is closed in a sealing manner by the closure plug element 11. The inner shaft portion 10a is moreover spread wider, and as a result the shaft 3 is clamped in sealing fashion in the collar element 10.

Figure 6:
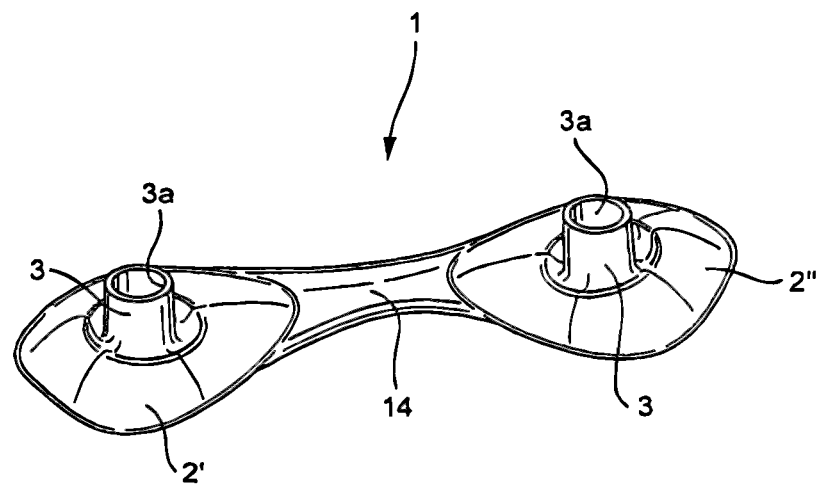
FIG. 6 is a perspective view illustrating a double-pad variant of the forehead-contacting device according to another embodiment of the invention.

FIG. 6 shows a variant of the forehead-contacting device 1 which has two jacket portions 2' and 2" that are adapted to receive a viscous medium, e.g., gel. The two jacket portions 2', 2" may be coupled to one another via a central connecting rib 14. The central rib 14 is structured such that in the application position of the forehead-contacting device, the central rib 14 does not rest, or does not rest excessively forcefully, on the region of the forehead of the user. In an exemplary embodiment, the unmolding of the mold core, intended for forming the interior of the jacket portions 2', 2", may be done by pulling the mold core out of the applicable inner opening 3a in the respective shaft portions 3.

Figure 7:
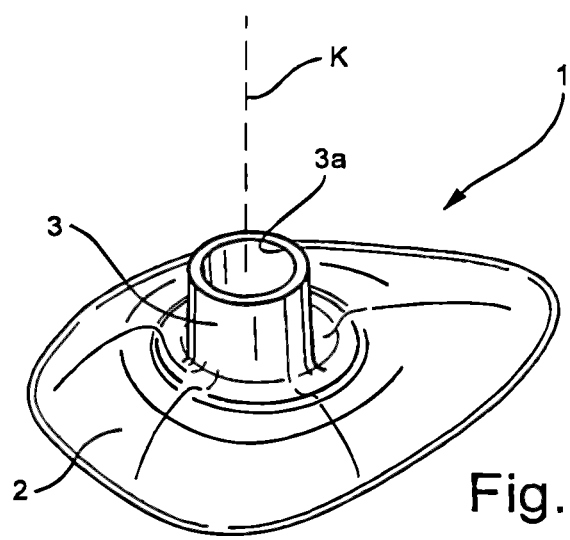
FIG. 7 is a perspective view illustrating a variant of the forehead-contacting device with a jacket of essentially crescent-shaped contour according to another embodiment of the invention.

FIG. 7 shows a further variant of the support element 1. In this exemplary embodiment, the jacket 2 is non-round, when viewed along the primary axis K. In particular, the jacket 2 is contoured polygonally or in crescent-shaped fashion. The unmolding of a mold core, intended for forming the interior of the jacket 2, may be done by elastically widening the shaft portion 3 via the shaft conduit 3a provided by the shaft portion 3.

Figure 8:
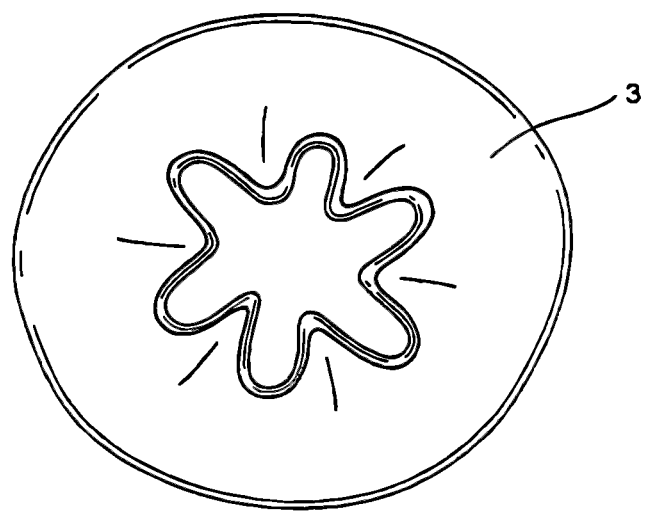
FIG. 8 is a plan view illustrating a concept for furnishing a more easily widenable neck or shaft portion of the jacket according to another embodiment of the invention.

FIG. 8 shows a variant of the shaft portion 3 in which the shaft portion is structured in "curly" or serpentine fashion, e.g., contoured in the shape of a star. This structure makes it possible to increase the effective length of the circumferential wall that forms the shaft portion 3, and as a result, without increasing the diameter of the circle outlining the shaft portion 3, to temporarily furnish a larger opening for the process of unmolding the mold core.

FIG. 9 illustrates a breathing mask 20 including a forehead contacting device with a support element 1 such as those described above. Further details of the breathing mask are described in WO 2003/035156, which is incorporated herein by reference in its entirety.

Aspects of the invention are not limited to the exemplary embodiments described above. For example, it is possible to close the jacket 2 and in particular the shaft portion 3 in some other way, e.g., glue it. It is also possible to supply a cross-linking agent to the gel introduced into the jacket 2, so that in the region of the shaft portion 3, this gel forms a sufficiently well-sealing closure stopper.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A method for forming a forehead-contacting device, comprising:
   molding a support element from an elastomer material that includes a jacket defining a hollow chamber and a hollow support shaft portion, the jacket and the hollow support shaft portion being formed from one continuous piece of the elastomer material;
   filling the hollow chamber with a viscous medium via the hollow support shaft portion;
   forming the jacket using a mold core tool; and
   unmolding the mold core tool via an inner conduit provided by the hollow support shaft portion of the jacket.

2. The method of claim 1, wherein the viscous medium comprises a gel.

3. The method of claim 1, further comprising closing the hollow chamber of the jacket with a closure device after the filling.

4. The method of claim 1, further comprising closing the hollow chamber by gluing the hollow support shaft portion closed.

5. The method of claim 1, further comprising closing the hollow chamber by clamping the hollow support shaft portion of the jacket with a collar element.

6. The method of claim 1, further comprising closing the hollow chamber by supplying a cross-linking agent to the viscous medium to form a closure stopper of the hollow support shaft portion.

7. The method of claim 1, wherein unmolding the mold core tool comprises pulling the mold core tool out along the inner conduit of the hollow support shaft portion of the jacket.

8. The method of claim 1, wherein unmolding the mold core tool comprises blowing the jacket out from the mold core tool using a pressure medium.

9. The method of claim 1, wherein unmolding the mold core tool comprises filling the hollow chamber with the viscous medium such that the jacket is positively displaced from the mold core tool.

10. The method of claim 1, wherein unmolding the mold core tool comprises elastically widening the shaft hollow support portion via the inner conduit.

11. The method of claim 1, further comprising:
    forming an annular bead about the hollow support shaft portion; and
    fixing a support plate element to said annular bead.

12. The method of claim 1, wherein the hollow support shaft portion is structured to connect to a forehead support of a breathing mask.

13. The method of claim 1, wherein the jacket is shaped to conform to a patient's forehead.

14. The method of claim 1, wherein the one continuous piece of the elastomer material is homogeneous.

15. A method for forming a forehead-contacting device, comprising:
    molding a support element from an elastomer material that includes a jacket defining a hollow chamber and a hollow support shaft formed in one piece with the jacket, by which the hollow chamber is adapted to be supported on a forehead support;
    attaching a collar element to the hollow support shaft provided to the jacket;
    inserting a closure plug element including a core conduit at least partway into the collar element and the hollow support shaft;
    filling the hollow chamber with a viscous medium via the hollow support shaft and the core conduit of the closure plug element; and
    further inserting the closure plug element into the hollow support shaft and the collar element to close the core conduit and hence close the hollow chamber and the hollow support shaft of the jacket.

16. The method of claim 15, wherein the viscous medium comprises a gel.

17. The method of claim 15, further comprising evacuating the hollow chamber via the core conduit before filling the hollow chamber with a viscous medium.

18. The method of claim 15, further comprising:
    forming the jacket using a mold core tool; and unmolding the mold core tool via an inner conduit provided by the hollow support shaft of the jacket.

19. The method of claim 15, further comprising:
   forming an annular bead about the hollow support shaft; and
   fixing a support plate element to said annular bead.

20. The method of claim 18, wherein unmolding the mold core tool comprises pulling the mold core tool out along the inner conduit of the hollow support shaft of the jacket.

21. The method of claim 18, wherein unmolding the mold core tool comprises blowing the jacket out from the mold core tool using a pressure medium.

22. The method of claim 18, wherein unmolding the mold core tool comprises filling the hollow chamber with the viscous medium such that the jacket is positively displaced from the mold core tool.

23. The method of claim 18, wherein unmolding the mold core tool comprises elastically widening the hollow support shaft via the inner conduit.

* * * * *